United States Patent [19]

Kanda et al.

[11] Patent Number: 4,602,505
[45] Date of Patent: Jul. 29, 1986

[54] APPARATUS FOR MEASURING VISCOSITY

[75] Inventors: Mamoru Kanda, Tokyo; Osamu Suzuki, Kumagaya; Shousuke Ishiwata, Saitama; Mitsuroh Hayashi, Kumagaya, all of Japan

[73] Assignee: Chichibu Cement Kabushiki Kaisha, Tokyo, Japan

[21] Appl. No.: 559,948

[22] Filed: Dec. 9, 1983

[30] Foreign Application Priority Data

Dec. 13, 1982 [JP] Japan ................. 57-218054

[51] Int. Cl.⁴ .................................... G01N 11/00
[52] U.S. Cl. .................................... 73/54; 73/579
[58] Field of Search .................. 73/54, 590, 579

[56] References Cited

U.S. PATENT DOCUMENTS

| | | | |
|---|---|---|---|
| 2,716,887 | 9/1955 | Smith | 73/795 |
| 3,449,940 | 6/1969 | Banks | 73/54 X |
| 3,608,715 | 9/1971 | Snyder et al. | 73/590 X |
| 4,327,587 | 5/1982 | Docekal et al. | 73/590 |

FOREIGN PATENT DOCUMENTS 3149909 6/1983 Fed. Rep. of Germany ......... 73/54

*Primary Examiner*—Kenneth M. Schor
*Attorney, Agent, or Firm*—Robert E. Burns; Emmanuel J. Lobato; Bruce L. Adams

[57] ABSTRACT

An apparatus for measuring the viscosity of a viscous substance as a sample to be measured has a tuning fork type vibrator having two vibrating plates opposing to each other at a distance. These vibrating plates are vibrated at equal frequencies in inversed phase relation to each other by means of a variable vibration generator. The vibrating members have thin plate-like sensitive members provided at their respective lower ends. An amplitude obtained by immersing the sensitive members in a viscous substance and vibrating the former is detected by a pickup device to detect a change in amplitude according to the viscous resistance of the viscous substance thereby to measure the viscosity thereof. The viscosity measuring apparatus has means for regulating the frequency of the vibration generator so as to vary the frequency according to need. Thus, when the relationship between viscosity and responsive vibration no longer maintains a substantially linear relationship at a predetermined driving frequency, the setting of the driving frequency is renewed, thereby allowing viscosity to be measured over a wide range and with a high accuracy.

4 Claims, 6 Drawing Figures

FIG. I
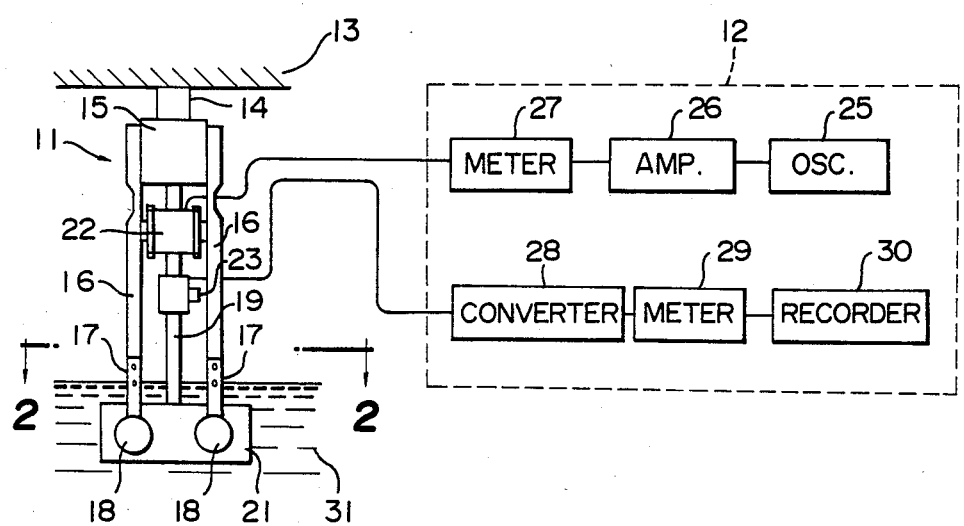
FIG. 2
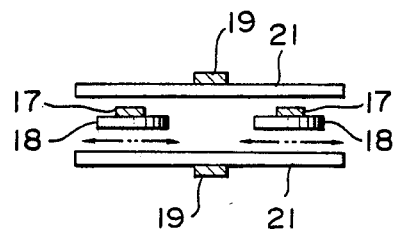

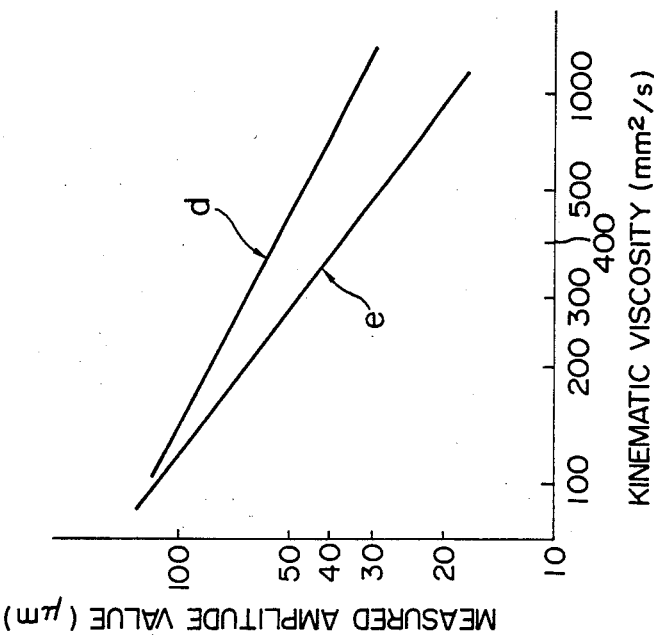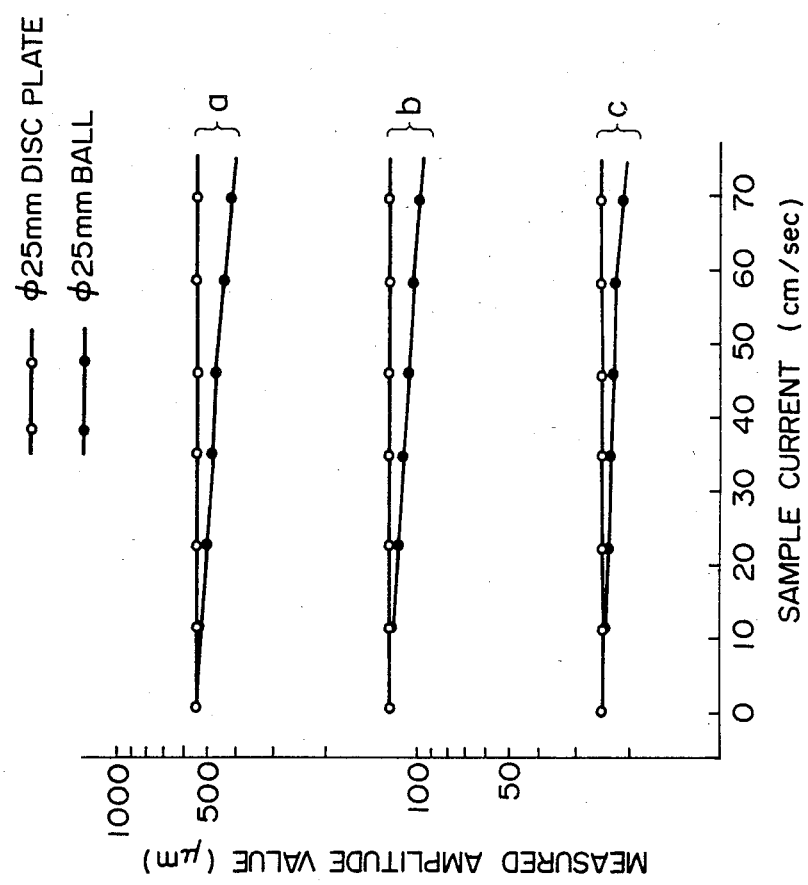

APPARATUS FOR MEASURING VISCOSITY

BACKGROUND OF THE INVENTION

The present invention relates to an apparatus for measuring the viscosity of a viscous substance, and more particularly to, a vibration-type viscosity measuring apparatus in which sensitive members are immersed in a viscous substance and subjected to a specific vibration, and the responsive amplitude of the sensitive members is detected to measure the viscosity of the viscous substance.

One type of viscosity measuring apparatus heretofore proposed has a tabular member which is immersed in a viscous substance and vibrated with a predetermined driving power, and the viscous resistance encountered by the tabular member is detected to measure the viscosity of the viscous substance. In such a vibration-type vicosity measuring apparatus, if the vibrating part is not completely fixedly supported the, measured values are inaccurate thereby resulting in variations in the results of the measurement. Accordingly, the assignee of the present applicantion has previously proposed in Japanese Patent Laid-Open No. 107881/1978 a viscosity measuring apparatus in which two opposing vibrating plates are vibrated at equal frequencies in inverse phase relation to each other for overcoming the above-mentioned disadvantage. By such as apparatus, the reactions of the vibrating plates are constantly cancelled with each other, and it becomes unnecessary to give special consideration to the supporting means for the vibrating plates, so that the results of measurement can be made stable at all times. Although the above-mentioned viscosity measuring apparatus has solved the problem of retaining the vibrating plates, when the driving frequency deviates from the resonance frequency, the responsive amplitude value of the vibrating plates sharply attenuates so as to make it impossible to effect measurement, which is characteristic of a tuning fork mechanism constituted by two vibrating plates. Also when the relationship between viscosity and responsive amplitude no longer maintains a substantially linear relationship, measurement cannot be performed.

Accordingly, the assignee of the present applicantion has proposed in Japanese Patent Laid-Open No. 135337/1982 a novel viscosity measuring method improved to overcome the above-mentioned disadvantages. More specifically, the method makes it possible to measure even a viscous substance having a small viscosity in such a way that in a viscous substance whose viscosity within a certain range is known, the resonance frequency of the vibrating plates measured when the viscosity is lowest is previously obtained, and the vibrating plates are driven at the resonance frequency. Moreover, when the viscous substance increases in viscosity so that the relationship between responsive amplitude and viscosity no longer maintains a substantially linear relationship, the driving frequency of the vibrating plates is changed to the resonance frequency of the viscous substance at that time to set a new substantially linear relationship. When the relationship between viscosity and responsive amplitude has deviated from the new substantially linear relationship, the above-mentioned operation is repeated. By so doing, continuous viscosity ranges are determined where viscosity and responsive amplitude have a substantially linear relationship. Then, to which viscosity range a viscous substance whose viscosity is unknown belongs is detected to drive the vibrating plates at a resonance frequency corresponding to the viscosity range and obtain the responsive amplitude thereof, thereby allowing a measurement of viscosity over a wide range. In this measuring method, however, it has been discovered that since each vibrating plate is constituted by a ball, a turbulent flow occurs at the interface thereof thereby making it impossible to obtain a high accuracy. Moreover, it has been found that when a viscous substance is measured in a fluid state, errors are inconveniently produced in the relationship between viscosity and responsive amplitude owing to fluid resistance.

SUMMARY OF THE INVENTION

Accordingly, a primary object of the present invention is to provide an apparatus for measuring viscosity with a high accuracy even when a viscous substance to be measured is in a fluid state, thereby overcoming the above-mentioned disadvantages of the prior art.

To this end, according to the present invention, there is provided an apparatus for measuring viscosity comprising: a tuning fork type vibrator having two vibrating plates which are opposed to each other and spaced apart a suitable distance; a vibration generator adapted to vibrate these vibrating plates at equal frequencies in inverse phase relation to each other, the vibration generator being variable in frequency; thin plate-like sensitive members attached to the lower ends of the vibrating plates, respectively, and disposed so that their planes are parallel to the direction of vibration of the vibrating plates; a pickup device for detecting an amplitude obtained by immersing the sensitive members in a sample to be measured and vibrating the former; and a regulator for regulating the driving frequency of the vibration generator.

According to a preferred embodiment of the invention, two static plates are provided so that their planes extend in parallel to the planes of the two sensitive members and the plates are disposed on both sides of the two sensitive members at a predetermined distance. Each of the static plates has an area sufficient for covering the two sensitive members.

In the viscosity measuring apparatus of the invention, a pair of sensitive members are vibrated in inverse phase relation to each other in the direction parallel to their planes. For this reason, a viscous substance, as a sample, at the interfaces of the thin plate-like sensitive members forms a laminar flow, so that the measuring accuracy is improved, and even when the viscous substance is in a fluid state the sensitive members can measure without meeting with any fluid resistance. Moreover, the viscosity measuring apparatus of the invention has means for regulating the driving frequency of the vibration generator. Therefore, when a sample to be measured changes in viscosity so that the relationship between responsive amplitude and viscosity no longer maintains a substantially linear relationship, the frequency of the vibrating plates can be immediately set to the resonance frequency of the viscous substance at that time. Accordingly, it is possible to measure viscosity over a wide range. In addition, the provision of the static plates makes it possible to detect the relationship between viscosity and amplitude value of a sample to be measured with a large gradient, so that it becomes possible to measure viscosity with a higher accuracy.

The above and other objects, features and advantages of the invention will become clear from the following description of the preferred embodiment thereof taken in conjunction with the accompanying drawings.

BRIEF DESCRIPTION OF THE DRAWINGS

FIG. 1 shows an embodiment of the apparatus for measuring viscosity in accordance with the invention;

FIG. 2 is a sectional view taken along the line 2—2 of FIG. 1;

FIG. 3 is a graph showing the relationship between the sample current and the measured amplitude value;

FIG. 4 is a graph showing the effect obtained when static plates are provided;

DESCRIPTION OF THE PREFERRED EMBODIMENT

Figure 6:
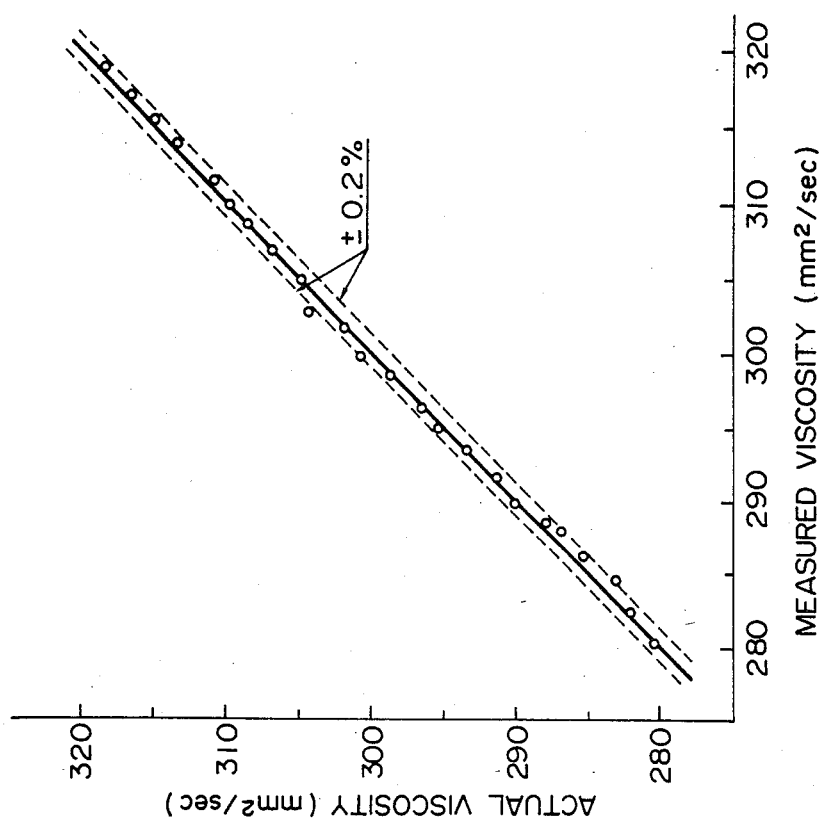
FIG. 6 is a graph showing the viscosity measuring accuracy by the apparatus in accordance with the invention.

An embodiment of the apparatus for measuring viscosity in accordance with the invention will be described hereinunder with specific reference to FIGS. 1 and 2. The apparatus is constituted by a vibrator body generally shown by a reference numeral 11 and a measuring unit surrounded with dotted line and shown by a reference numeral 12. The vibrator body 11 has a base 15 attached to the underside of a supporting frame 13 through a spacer 14. To opposite sides of the base 15 are attached the upper ends of leaf spring-like vibrating plates or vibratable arms 16 which in combination constitute a tuning fork type vibrator. The vibrating plates or arms 16 are provided at their lower ends with circular or oval thin plate-like sensitive members or disks 18 through mounting plates 17, respectively. The sensitive members 18 are also vibrating plates and disposed so that their planes are parallel to the direction of vibration of the vibrating plates 16, i.e., perpendicular to the planes of the vibrating plates 16. To the other opposite sides of the base 15 are attached the upper ends of respective supporting members 19 having a high strength. The lower end of each supporting member 19 extends to the vicinity of the mounting plates 17. The supporting members 19 have rectangular static plates 21 attached to their lower ends, respectively. These static plates 21 are disposed such that the above-mentioned sensitive members 18 are located in the central part or space between the plates 21. In addition, the static plates 21 have an area sufficient for the sensitive members 18 to be located therebetween during vibration of the vibrating plats 16. A known electromagnetic coil-driven vibration generator 22 is attached to the upper parts of the supporting members 19. The vibration generator 22 is adapted to vibrate the two vibrating plates 16 at equal frequencies in inverse or opposite phase relation to each other. The direction of the vibration is horizontal as viewed in FIG. 1. The vibration generator 22 may be constituted by a known magnetostrictive or electrostrictive vibrator. A pickup 23 is attached to the supporting member 19 below the vibration generator 22 for detecting the amplitude of the vibrating plates 16. The pickup 23 is constituted by, e.g., an electromagnetic amplitude detector that takes out a change in amplitude of the vibrating plates 16 as a change in magnetism for detecting the same as a change in current, or a photoelectric amplitude detector that takes out a change in amplitude of the vibrating plates 16 as a change in quantity of light for detecting the same as a change in current. The amplitude detector may be constituted by an amplitude detector utilizing a magnetostrictive or electrostrictive effect.

The measuring unit 12 is composed of a resonance section and an indicator section. The resonance section has an oscillator 25, an amplifier 26 that amplifies the output signal from the oscillator 25, and a setting meter 27 that displays the output value from the amplifier 26 by means of a frequency scale and includes adjusting means, such as a variable resistor, for adjustably setting the frequency to a desired value, the output of the setting meter 27 being connected to the vibration generator 22. On the other hand, the indicator section has a converter 28 that converts the output signal from the pickup 23 to a corresponding current signal; a meter 29 adapted to permit the output signal from the converter 28 to be read on a viscosity scale, and a recorder 30 that automatically records the value on the meter 29.

The measurement by means of this viscosity measuring apparatus is effected as follows. The vibrator body 11 is held so that the sensitive members 18 and the static plates 21 are immersed in a viscous substance 31 to be measured, and then the vibration generator 22 is driven. At this time, a predetermined exciting force level is set by means of the setting meter 27. By the operation of the vibration generator 22, the two vibrating plates 16 are vibrated in a stationary manner, so that also the sensitive members 18 connected to these vibrating plates 16 are vibrated in the viscous substance 31 as shown by arrows in FIG. 2. The vibration of the sensitive members 18 changes the amplitude of vibration of the vibrating plates 16 according to the viscous resistance of the viscous substance 31. The change in amplitude is detected by means of the pickup 23 and converted to an electrical value in the converter 28. The output of the converter 28 actuates the meter 29 to indicate the same as the viscosity of the viscous substance 31. When the viscosity of the viscous substance 31 increases so that the relationship between viscosity and responsive amplitude no longer maintains a substantially linear relationship at the driving frequency set by means of the setting meter 27, the setting of the driving frequency is adjusted by means of the setting meter 27. By so doing, the viscosity of the viscous substance can be measured over a wide range and with a high accuracy.

The following is the description of an experimental example for explaining an advantageous effect offered by the viscosity measuring apparatus in accordance with the invention. The graph of FIG. 3 shows results obtained when a viscous substance to be measured is in a fluid state. In this example, two kinds of shape of the sensitive members 18 were prepared: a disc plate having a thickness of 0.6 mm and a diameter of 25 mm; and a ball having a diameter of 25 mm. Employed samples were three aqueous glycerin solutions different in viscosity from each other: (a) an aqueous solution having a glycerin content of 56.5%; (b) an aqueous solution having a glycerin content of 82.4%; and (c) an aqueous solution having a glycerin content of 95.6%. Also, the samples were subjected to change in speed of flow or current. More specifically, the speed or current of the samples was changed from zero in a stationary state to 70 cm/sec to measure amplitude values of the samples. It will be understood from FIG. 3 that as compared with the sensitive members 18 constituted by the balls, those constituted by the disc plates hardly have a reduction in amplitude value with changes in the sample current, i.e., the disc plate-like sensitive members 18 provide a constant amplitude value so that the same measuring accuracy as that in a stationary state of the sample can be obtained even in a fluid state.

FIG. 4 is a graph showing results of examination of the effect of the static plates 21 carried out by employing a viscosity standard liquid having a constant viscosity as a sample viscous substance. A straight line (d) represents the relationship between the measured amplitude value of the sensitive members 18 and the kinematic viscosity obtained in the case where the vibrating plates 16 are driven at a frequency of 37.4 Hz with an exciting force of 42.5 mA, with no static plates 21 provided. On the other hand, another straight line (e) expresses the relationship, similar to that shown by the straight line (d), obtained in the case where the vibrating plates 16 are driven at a frequency of 42.5 Hz with an exciting force of 45.5 mA and the static plates 21 are provided. It will be clear from FIG. 4 that a steeper gradient can be obtained in the relationship between viscosity and the responsive amplitude value in the case where the static plates 21 are provided. As the straight line is steeper in gradient, the change in the responsive amplitude value can be read more accurately, so that it becomes possible to measure viscosity with a higher accuracy. It has been found that in this case it is preferable to make the gap between the static plates 21 wide at a high viscosity but narrow at a low viscosity. Therefore, it is preferable to cut the supporting members 19 at the portions thereof below the pickup 23 and support the cut-off portions of the supporting members 19 so that the gap therebetween is adjustable. More specifically, if an expansion member which can be expanded and contracted through regulation by means of a screw, such as a pantograph, is attached to the lower part of the pickup 23 and the lower supporting members are secured to the expansion member, then the gap between the two supporting members is made adjustable. Moreover, it has been found that the provision of only one of the static plates 21 is still more effective than the case where no static plates 21 are provided.

Figure 5:
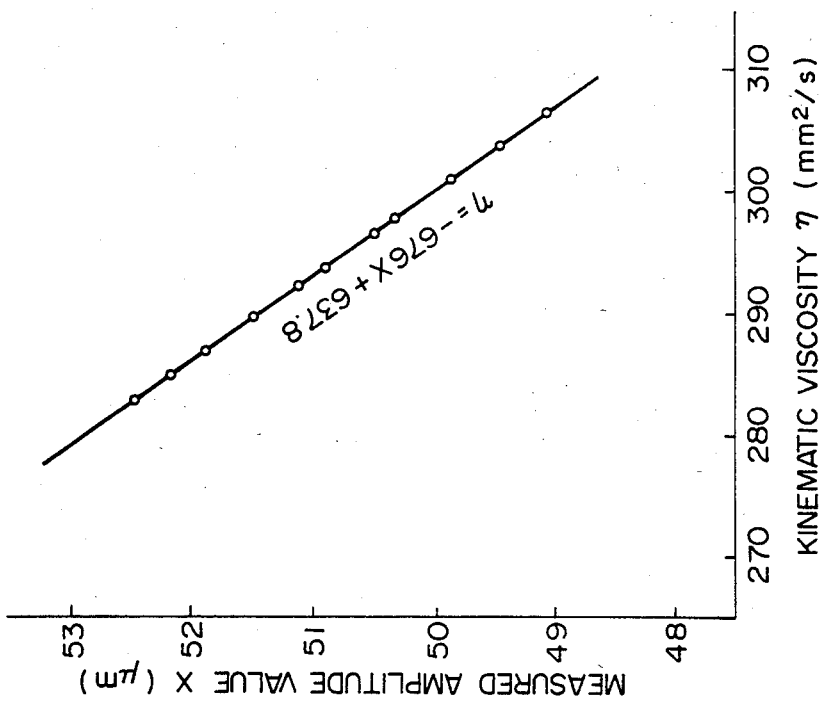
FIG. 5 is a graph showing the relationship between the measured amplitude value and the kinematic viscosity.

FIG. 5 is a graph showing the relationship between the measured amplitude value and the kinematic viscosity obtained by measuring the change in kinematic viscosity of a viscosity standard liquid over a range between 280 and 310 mm²/sec in the case where a calibration curve is prepared by the viscosity measuring apparatus of the invention. The relationship is expressed by the following approximate linear equation:

$$\eta = -6.76 X + 637.8$$

where $\eta$ represents the kinematic viscosity (mm²/sec), and X the measured amplitude value ($\mu$m).

By this calibration curve equation, the viscosity can be easily obtained from the measured amplitude value.

FIG. 6 is a graph showing results of the examination of the accuracy in measurement of viscosity by the above-mentioned calibration curve equation. In the graph, the measured viscosity is compared with the actual viscosity. More specifically, in the graph, a solid line represents the actual viscosity, while the dotted lines express the upper and lower limits of results of measurement carried out by employing the apparatus of the invention, respectively. It has been confirmed from the results shown in FIG. 6 that measurement can be effected with an accuracy within a range of ±0.2% and the accuracy is higher than that in the case where no static plates are provided.

It is to be noted that the static plates 21 may be replaced with a box-like structure capable of accommodating the two sensitive members 18, and a viscous substance as a sample may be placed therein to perform measurement. Such an arrangement is effective when it is desired to know the change in viscosity of a viscous substance with a change in temperature, for example, since the amount of a sample is small so that the sample is raised to a predetermined temperature within a short period of time, i.e., the measuring time is reduced.

Although the invention has been described through specific terms, it is to be noted here that the described embodiment is not exclusive and various changes and modifications may be imparted thereto without departing from the scope of the invention which is limited solely by the appended claims.

What is claimed is:

1. An apparatus for measuring viscosity comprising:
   a base member;
   a tuning fork vibrator including two vibrating plates each having upper and lower ends, the two vibrating plates being mounted on the base member at the upper ends thereof and being disposed in opposed spaced apart relation from each other;
   a vibration generator supported by the base member for vibrationally driving the vibrating plates to vibrate at the same vibrational frequency in opposite phase relation, the vibration generator having a variable vibrational frequency;
   two vibration-sensitive members comprised of thin plates, each thin plate being attached to the lower end of a respective one of the vibrating plates to undergo vibration therewith and each thin plate having a pair of major surfaces arranged in parallel with the direction of vibration of the vibrating plates;
   a pickup device mounted on the base member for detecting an amplitude of vibration of the vibrating plates obtained by immersing the two thin plates into a sample to be measured and for converting the detected amplitude into an electrical signal representative of the viscosity of the sample; and
   adjusting means for regulating the driving frequency of the vibration generator.

2. An apparatus for measuring viscosity according to claim 1; further comprising two static plates supported by the base member and disposed on opposite sides of the two thin plates at a predetermined spaced-apart distance, each of the static plates having a pair of surfaces extending parallel to said surfaces of the thin plates and having an area sufficient to cover the two thin plates during vibration thereof.

3. An apparatus for measuring viscosity according to claim 1; further comprising a meter coacting with the adjusting means for providing an indication of the driving frequency on a frequency scale.

4. An apparatus for measuring viscosity according to claim 1; wherein the thin plates have a circular shape.

* * * * *